US007377782B1

(12) United States Patent
Brosnihan

(10) Patent No.: US 7,377,782 B1
(45) Date of Patent: May 27, 2008

(54) SYSTEM AND METHOD FOR REIMPLANTING AVULSED TEETH

(76) Inventor: James Brosnihan, 503 N. 38th St., Omaha, NE (US) 68131

(*) Notice: Subject to any disclaimer, the term of this patent is extended or adjusted under 35 U.S.C. 154(b) by 379 days.

(21) Appl. No.: 11/111,404

(22) Filed: Apr. 21, 2005

(51) Int. Cl.
*A61C 9/00* (2006.01)

(52) U.S. Cl. .................. 433/215; 433/6; 128/861

(58) Field of Classification Search .......... 433/6, 433/215; 128/859, 861, 862
See application file for complete search history.

(56) References Cited

U.S. PATENT DOCUMENTS

| 2,705,492 | A | * | 4/1955 | Chandler | ............... 128/862 |
| 2,755,552 | A | * | 7/1956 | Brandau | ............... 433/215 |
| 3,337,957 | A | | 8/1967 | Reed | ............... 32/14 |
| 3,675,327 | A | * | 7/1972 | Huget et al. | ............... 433/215 |
| 4,504,229 | A | * | 3/1985 | Garito et al. | ............... 433/215 |
| 4,802,853 | A | * | 2/1989 | Krasner | ............... 433/215 |
| 4,904,188 | A | * | 2/1990 | Baurmash | ............... 433/215 |
| 5,087,202 | A | | 2/1992 | Krenkel | ............... 433/215 |
| 5,184,955 | A | * | 2/1993 | Baer et al. | ............... 433/215 |
| 5,213,498 | A | * | 5/1993 | Pelerin | ............... 433/37 |
| 5,328,362 | A | * | 7/1994 | Watson et al. | ............... 433/6 |
| 5,800,175 | A | * | 9/1998 | Zuk et al. | ............... 433/217.1 |
| 6,231,337 | B1 | * | 5/2001 | Boyd | ............... 433/6 |
| 7,048,542 | B2 | * | 5/2006 | Von Arx et al. | ............... 433/215 |
| 2005/0022824 | A1 | * | 2/2005 | Ball | ............... 128/861 |

OTHER PUBLICATIONS

Gregg et al, "Treatment of Avulsed Permanent Teeth in Children," International Jounal of Paediatric Dentistry 1998; 8: 75-81.*

* cited by examiner

*Primary Examiner*—Ralph A Lewis
(74) *Attorney, Agent, or Firm*—Thomte Law Office; Dennis L. Thomte

(57) ABSTRACT

A system for reimplanting avulsed teeth includes a dental splint having a pre-shaped channel that releasably engages a dental arcade having one or more avulsed teeth. The avulsed teeth are reinserted into their sockets and the dental splint is positioned over the dental arcade. The dental splint is worn continuously until reattachment is substantially attained. One embodiment provides masticatory surfaces to the dental splint that assist a user in eating while wearing the dental splint. Another embodiment provides a resilient layer to an engagement surface of the dental splint, which conforms to and engages the dental arcade. Adhesives may be disposed between the dental splint and the dental arcade when necessary.

3 Claims, 5 Drawing Sheets

SYSTEM AND METHOD FOR REIMPLANTING AVULSED TEETH

BACKGROUND OF THE INVENTION

1. Field of the Invention

The present invention relates to methods of stabilizing traumatized teeth and more particularly to a system and method for reimplanting and stabilizing avulsed teeth using a dental splint that removably engages the dental arcade from where the tooth was avulsed.

2. Description of the Prior Art

Tooth avulsion occurs when an entire tooth is forcefully dislodged from its socket. This type of traumatic injury is quite common, especially among children. While it is possible to save an avulsed tooth, a rapid response with proper procedures and tooth care is crucial. If the periodontal membrane of an avulsed tooth has not been substantially damaged, and if the cells are still alive, the tooth can many times be successfully reimplanted in the socket. Several days must pass before the tooth can have a chance to naturally reaffix to the socket. Accordingly, several attempts at providing systems for stabilizing the traumatized tooth have been developed. However, these attempts have provided mixed results and require procedures that are not easily implemented by emergency medical personnel within the narrow opportunity for reimplanting the tooth.

One prior art dental splint is disclosed within U.S. Pat. No. 3,337,957. That particular device teaches the attachment of a plurality of separate plates to the labial surfaces of the crown portions of the traumatized tooth and the teeth on either side thereof. Each of the plates are provided with outwardly extending T-shaped lugs that are imbedded into an arched bar or wire, which secures the separate plates and the adjacent teeth to one another. Ligature wires are used to couple the plates to the individual teeth. Wire must be passed around each tooth and then twisted closed into a secure position. This prior art system is too complex and cumbersome for most emergency medical personnel to implement in the field or in an emergency room setting. Moreover, the system depends upon well-anchored adjacent teeth and does not easily lend itself to a situation where a plurality of teeth from a single location of the dental arcade are avulsed at once. Moreover, such a system may anchor a single avulsed tooth in a manner that prohibits even the slightest movement with respect to the socket and adjoining teeth. Unfortunately, minor amounts of movement can be important for promoting the healing process, favoring ligament growth and inhibiting bone tissue development adjacent the root.

A slightly improved but similar system is taught within U.S. Pat. No. 5,087,202. The system is comprised of a plurality of individual rings that are cemented to the crown of the avulsed tooth and the adjacent teeth. Elongated connecting bars are secured to the individual rings, locking the adjoined teeth to one another in a stable position. While this system is less labor intensive than previous systems, it still suffers from the shortcomings experienced previously, such as over-immobilization of the teeth, and providing an undesirable level of technical involvement between emergency medical personnel and the avulsed teeth.

Accordingly, what is needed is a system and method for reimplanting avulsed teeth that may be quickly and easily used by emergency medial personnel without complex and laborious custom fitting procedures. However, such a system and method should adequately stabilize the avulsed teeth, without over-immobilization of the same.

SUMMARY OF THE INVENTION

The system and method for reimplanting one or more avulsed teeth of the present invention is provided with a dental splint that is releasably secured to the dental arcade from which the teeth were avulsed. Once the avulsed teeth are reinserted into their respective sockets, the dental splint may be applied. A first surface of the dental splint is provided with a channel that is generally shaped and sized to releasably receive at least a portion of the dental arcade. The dental splint is retained in position until a generally firm reattachment of one or more of the avulsed teeth occurs. The dental splint is provided to be worn continuously, including those periods which involve eating, drinking and sleeping.

In a preferred embodiment, the dental splint is constructed to engage only one of the upper or lower arcades of teeth. The channel of the dental splint should be preformed to approximate a wide range of individuals. The channel should also be formed to extend a sufficient distance along the labial or buccal and lingual surfaces of the teeth in order to provide a position that is sufficiently secure to permit the user to eat and drink while wearing the dental splint without unintentionally uncoupling the same from the dental arcade. Where the user will not generally be able to apply periodic pressure to the dental splint, whether due to age or incapacity, a temporary dental adhesive may be applied within the channel to adhere the dental splint to the teeth.

In one preferred embodiment, a second surface of the dental splint, opposite the channel, is provided with a plurality of facets that face in a plurality of different directions so that an irregular surface is provided. The irregular surface may be shaped to generally mimic masticatory surfaces of teeth in order to enable a user to more easily chew food while the dental splint is being worn. In still another embodiment, the second surface of the dental splint may be comprised of a generally rigid material while the first surface and channel may be comprised of a generally resilient material. This configuration may provide a wider range of fitting opportunities for different individuals as well as provide a snug, custom fit.

It is therefore a principle object of the present invention to provide a method for reimplanting one or more avulsed teeth that incorporates the use of a removable dental splint.

A further object of the present invention is to provide a method for reimplanting one or more avulsed teeth that incorporates the use of a dental splint having a preshaped channel that can fit a wide array for different users.

Still another object of the present invention is to provide a method for reimplanting one or more avulsed teeth that incorporate the use of a dental splint which covers a substantial portion of a single dental arcade from which the one or more avulsed teeth originated.

Yet another object of the present invention is to provide a method for reimplanting one or more avulsed teeth that incorporates the use of a dental splint having an outwardly facing surface that is shaped to provide masticatory surfaces that may be used for chewing food.

A further object of the present invention is to provide a method for reimplanting one or more avulsed teeth that incorporates the use of a dental splint which covers a substantial portion of a dental arcade and uses a resilient upper layer that releasably engages the dental arcade.

Still another object of the present invention is to provide a method for reimplanting one or more avulsed teeth that may be quickly and easily implemented by emergency medical professionals or the injured individual.

Yet another object of the present invention is to provide a system for reimplanting one or more avulsed teeth that is relatively simple and inexpensive to manufacture.

These and other objects of the present invention will be apparent to those having skill in the art.

DESCRIPTION OF THE PREFERRED EMBODIMENT

In the following detailed description of exemplary embodiments, reference is made to accompanying FIGS. 1-8, which form a part hereof and show, by way of illustration, exemplary embodiments of the present invention. These embodiments are disclosed in sufficient detail to enable those skilled in the art to practice the invention. It is to be understood that other embodiments may be utilized, however, and other changes may be made without departing from the spirit or scope of the present invention. The following detailed description is, therefore, not to be taken in a limiting sense in that the scope of the present invention is defined only by the appended claims.

In a preferred embodiment, the method for reimplanting one or more avulsed teeth of the present invention is first provided with an avulsed tooth that remains a viable candidate for reimplantation. Preferably, the avulsed tooth has no substantial damage, particularly to the periodontal membrane and the root. It is contemplated that the reimplantation will be attempted within moments of the tooth becoming avulsed or within a couple of hours thereafter. While it is possible to reimplant a tooth that is properly cared for several hours after the initial injury, the chances for success decrease rapidly as time progresses. After proper inspection of an avulsed tooth 2, it may be reinserted within the socket 4 of the dental arcade 6 from which it came. Depending upon the condition of the socket 4 and the bone adjacent thereto, the avulsed tooth 2 should encounter slight resistance before "clicking" into place.

Figure 1:
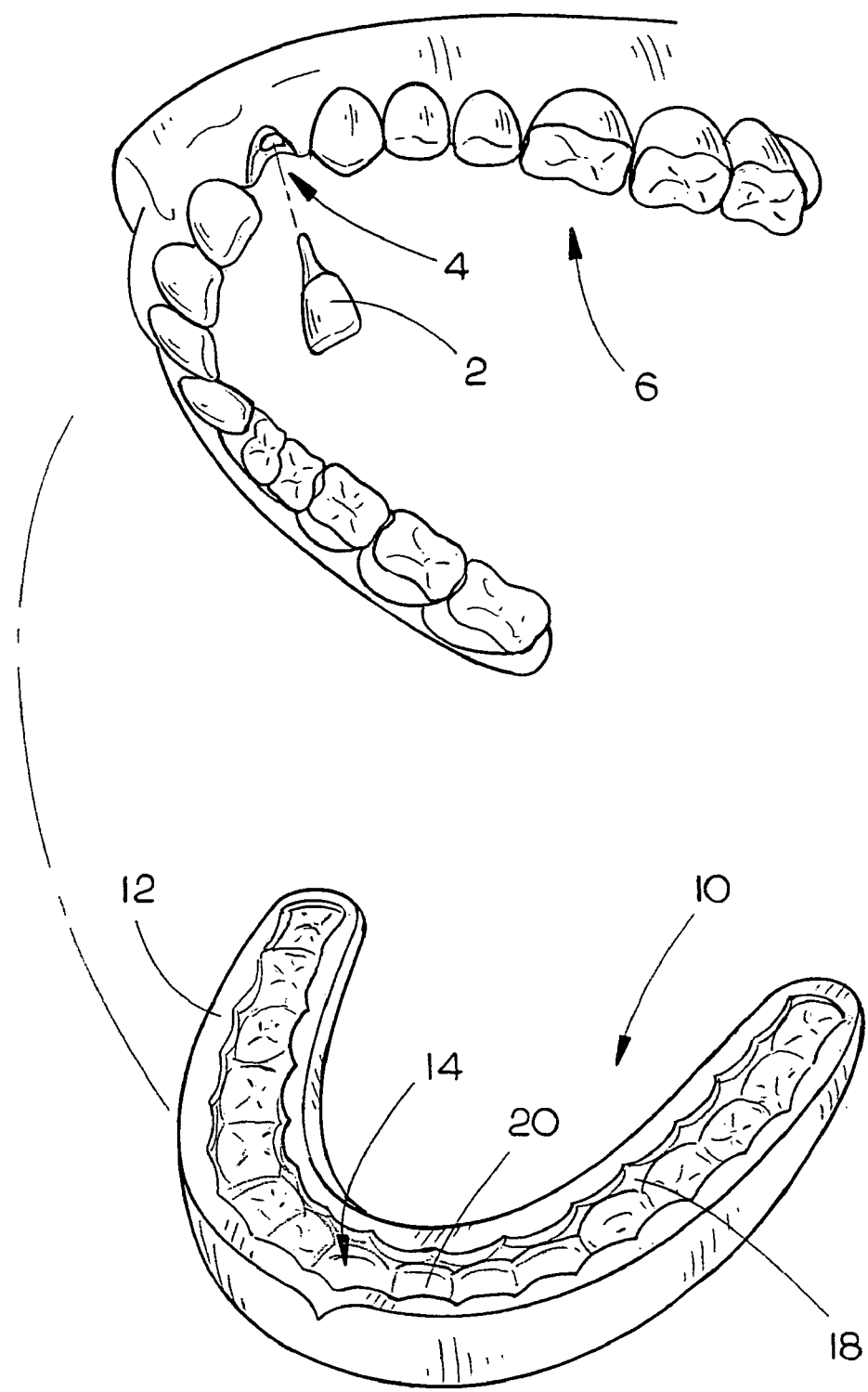
FIG. 1 is an isometric view of one preferred embodiment of the dental splint of the present invention.
Figure 2:
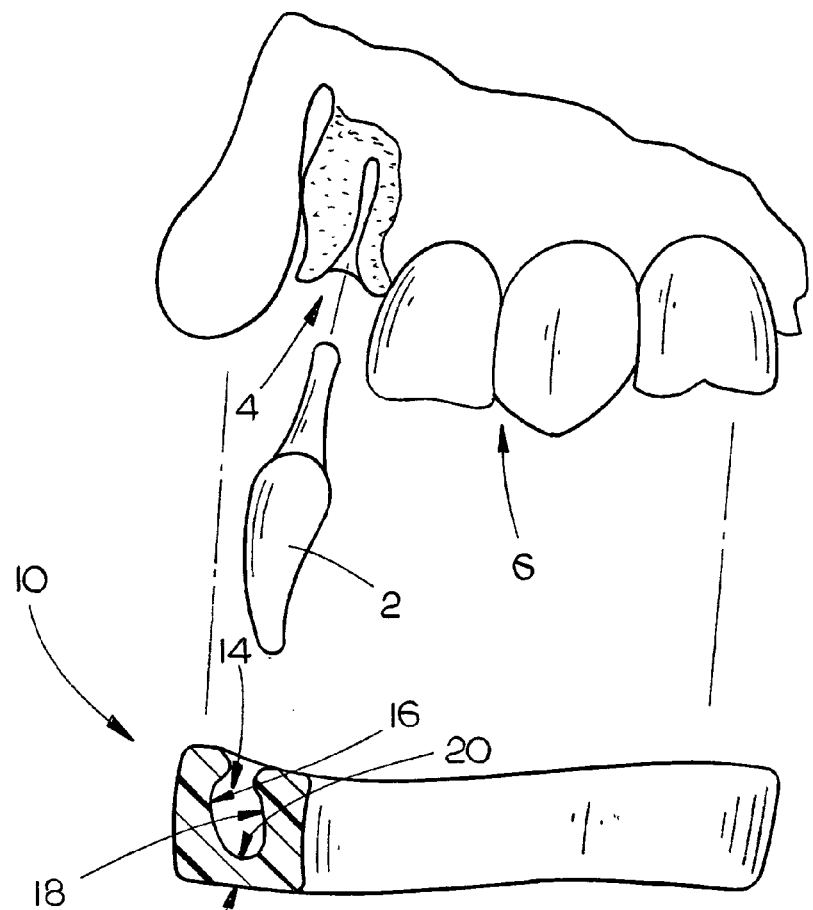
FIG. 2 is a partial, side elevation view of one embodiment of the dental splint of the present invention as the same may be positioned for use with a dental arcade having an avulsed tooth.
Figure 3:
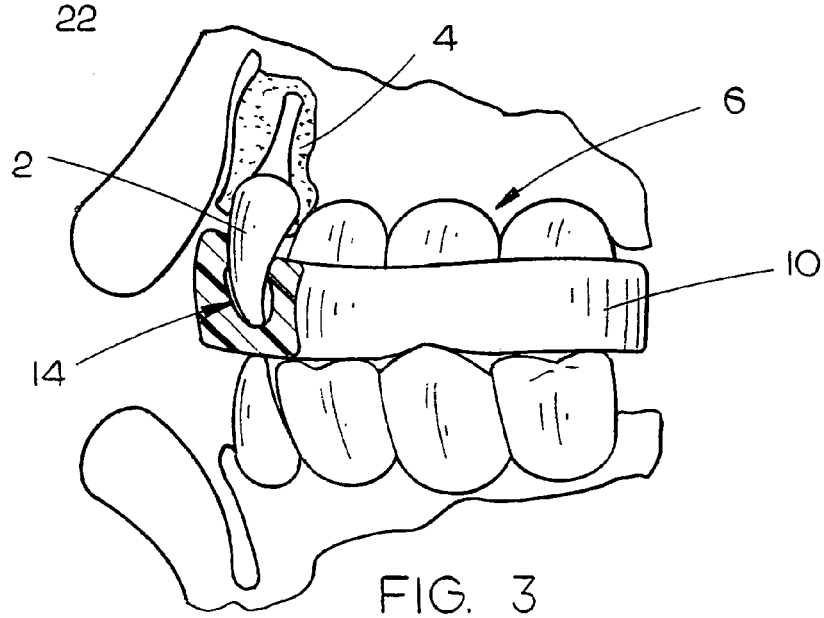
FIG. 3 is a partial, side elevation view of the dental splint of FIG. 2 as the same may be coupled with the dental arcade.
Figure 4:
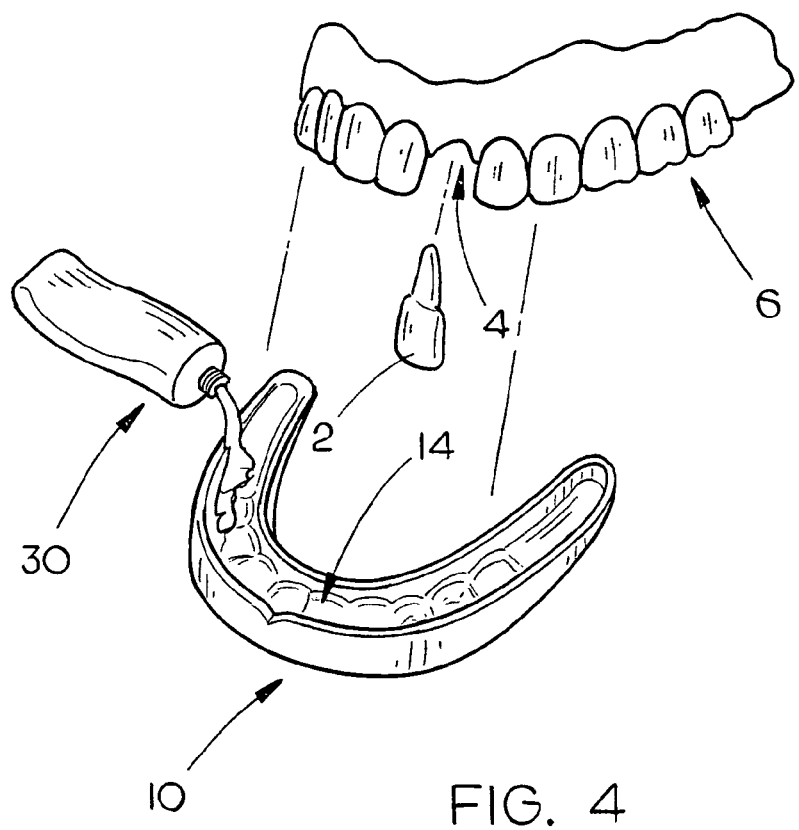
FIG. 4 is an isometric view of one embodiment of the dental splint of the present invention and one manner in which it might be used.
Figure 5:
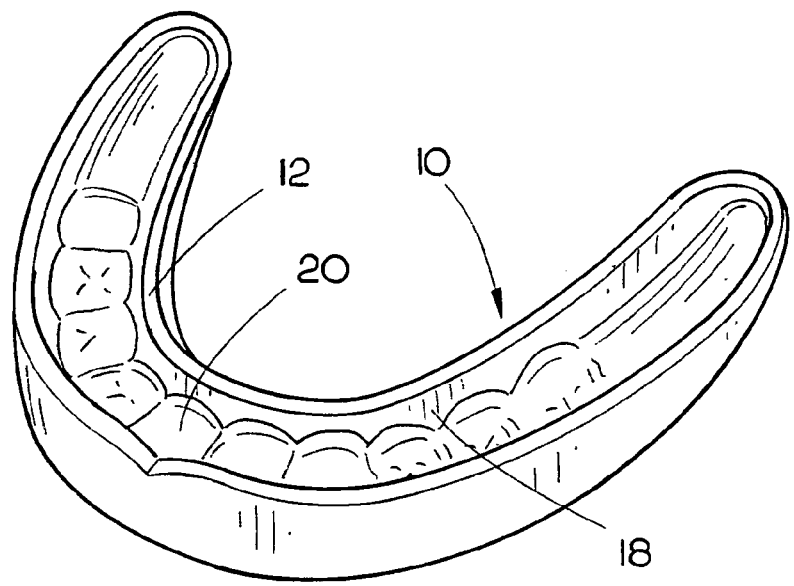
FIG. 5 is an isometric view of another embodiment of the dental splint of the present invention.

In a preferred embodiment, a dental splint 10 is provided for stabilizing the avulsed tooth 2. While the dental splint 10 will be described herein as it could be used with a single avulsed tooth, the dental splint 10 may be used for the simultaneous reimplantation of a plurality of teeth, whether the teeth adjoin one another or are spaced from one another. The dental splint 10 should be formed to have a first surface 12 having a channel 14 formed therein. As depicted in FIG. 1, the channel 14 should be shaped and sized to releasably receive at least a portion of an upper or lower arcade of teeth that includes the avulsed tooth 2. Accordingly, the channel 14 may be provided in a generally U-shape, depending upon the total area of the dental arcade that will be engaged with the dental splint 10. Generally opposite side walls are provided, consisting of a forward wall 16 that engages the lingual or buccal surfaces of the teeth and a rearward wall 18 that engages the lingual surface of the teeth. A bottom wall 20 extends between lower end portions of the forward wall 16 and rearward wall 18, engaging the masticatory surfaces of the teeth. It is contemplated that the dental splint 10 may be formed to engage substantially all of the dental arcade or only a portion thereof.

In one preferred embodiment, the dental splint 10 is fabricated from a generally rigid material that is appropriate for temporary use within a patient's mouth for a week or longer. Accordingly, several polymers, such as polypropylene, polyethylene and polyvinalchloride may be used. It is contemplated that the dental splint 10 will be provided in a plurality of different sizes that will closely fit individuals of various ages and having various sizes of dental arcades. Accordingly, the dental splints may be precast from several different size models. Preferably, the generalized fit will be such that at least one of a plurality of different sizes will fit the dental arcade of a particular individual in a manner that provides a secure frictional engagement between the channel 14 and the crowns of the individual teeth. In a preferred embodiment, the dental splint 10 is provided to engage only a single arcade of teeth, permitting the individual to eat and drink while the dental splint 10 is engaged with the dental arcade. While the dental splint 10 should be removably engaged with the dental arcade, it is contemplated that blood and foreign debris may become packed within small crevices of the channel 14 around the individual teeth and in particular the avulsed tooth 2. Therefore, if an individual were to attempt to remove a dental splint that covered both the upper and lower dental arcades simultaneously, the avulsed tooth 2 may be extracted from the socket 4, being cemented within the channel 14 by the blood and foreign debris.

Figure 6:
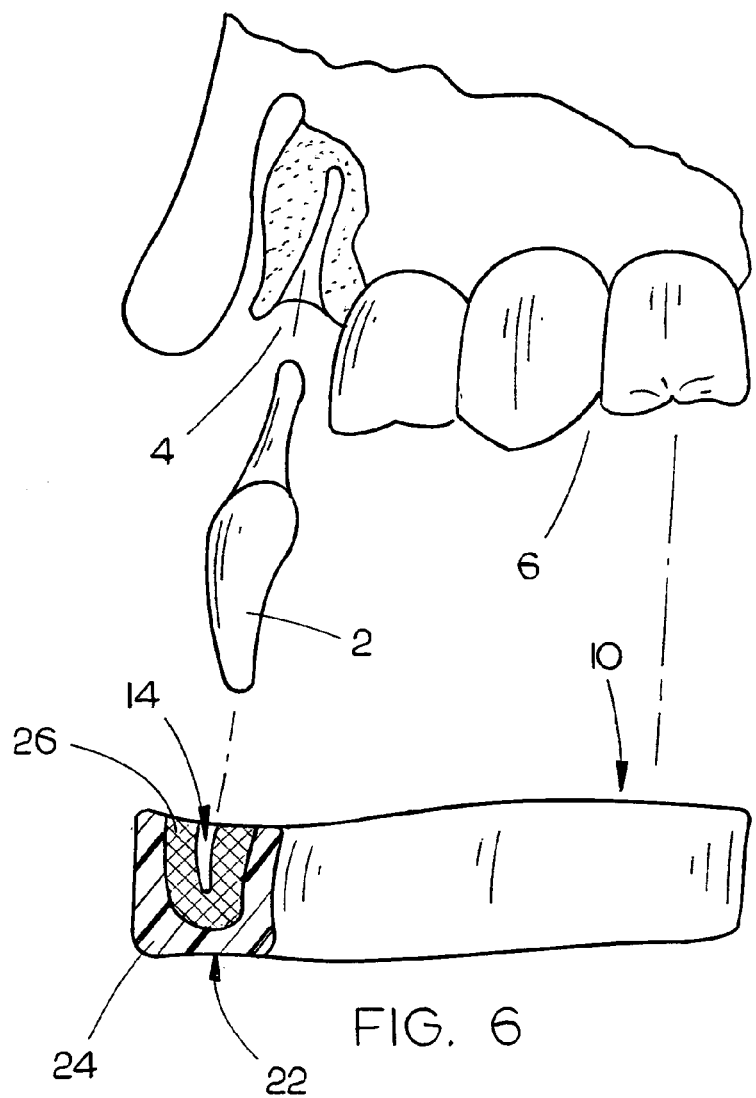
FIG. 6 is a partial, side elevation view of another embodiment of the dental splint of the present invention as the same may be positioned for use with a dental arcade having an avulsed tooth.
Figure 7:
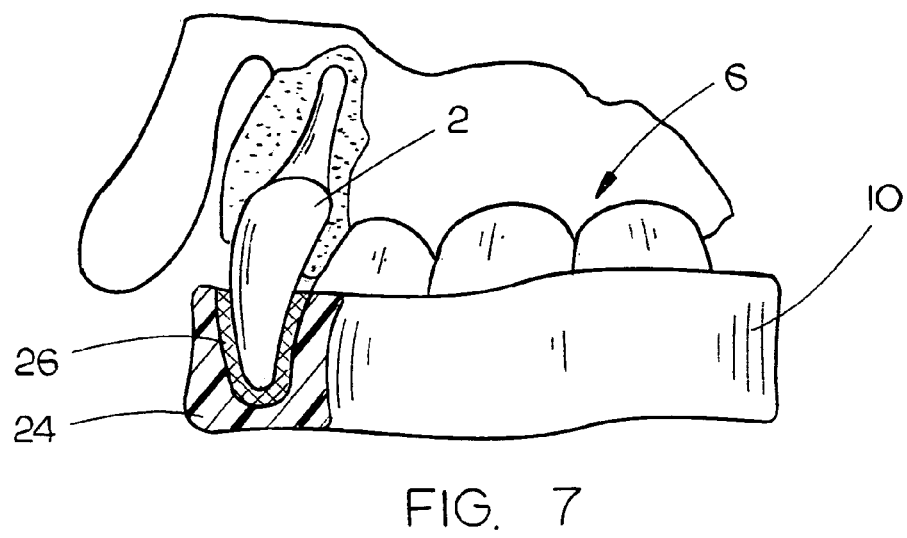
FIG. 7 is a partial, side elevation view of the dental splint of FIG. 6 as the same may be coupled with the dental arcade.

In another embodiment, depicted in FIGS. 6 and 7, the dental splint 10 may be formed to have at least two layers of different materials. A second surface 22 may be substantially comprised of a generally rigid material, such as a polymer of the types discussed previously herein. This generally rigid material will form a base layer 24 and may extend upwardly along the forward wall 16 and rearward wall 18. It is further contemplated that the base layer 24 may form a portion of the bottom wall 20. The first surface 12 of the dental splint 10 is comprised of a layer of deformably resilient material and defines a substantial portion of the groove 14. In this particular embodiment, the channel 14 will be simply viewed as a narrow slit when the dental splint 10 is not in use. When the dental splint 10 is engaged with the dental arcade, however, the resilient material will provide an engagement layer 26 that will closely conform to the shape of the individual teeth within the dental arcade. The resilient nature of the material will apply a slight gripping pressure on the surfaces of the teeth. Having the channel 14 formed into the engagement layer 26 will substantially prevent the layer of resilient material from pushing the dental splint 10 off of the dental arcade. It is contemplated that several different known materials may be used for the engagement layer 26. For example, different closed-cell foams of various rigidity or a resiliently deformable polymer or resin based material will be sufficient for most applications. The resilient material will permit the avulsed tooth 2 to move slightly in response to minor movements of the dental splint 10, thereby assisting in the healing of the area and the reimplantation of the tooth without permitting excessive movement.

It is contemplated that situations may arise where, due to the age or physical condition of the individual, the individual may have difficulty maintaining the dental splint 10 in an engaged position with the dental arcade 6. Accordingly, a temporary dental adhesive 30 may be applied between the dental arcade 6 and the channel 14. It is preferred, however, that the adhesive be applied to those areas of the channel 14 that will not come into contact with the avulsed tooth 2. Even after a generally firm reattachment of the avulsed tooth 2 is achieved, removal of the dental splint 10, with the avulsed tooth 2 adhered thereto, may cause the unwanted loosening or extraction of the avulsed tooth 2.

Figure 8:
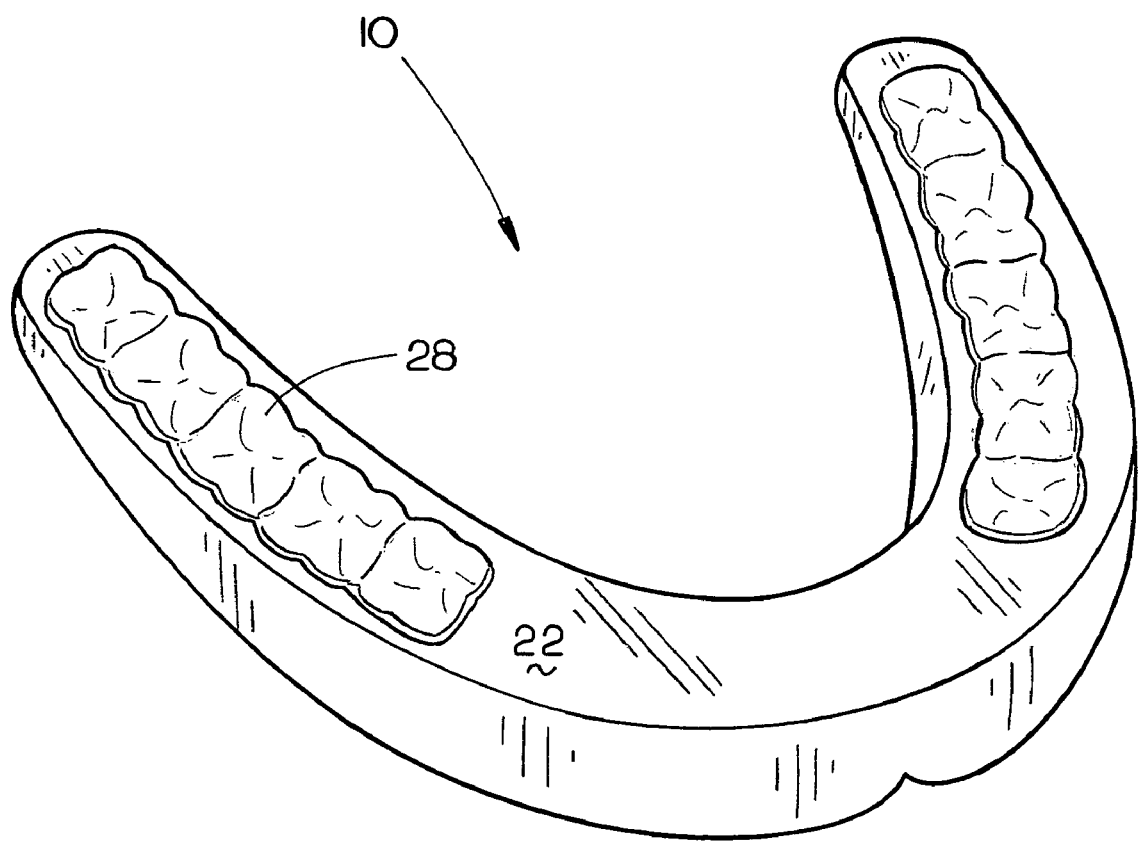
FIG. 8 is a bottom isometric view of still another embodiment of the dental splint of the present invention.

In still another embodiment of the dental splint 10, the second surface 22 may be provided with a plurality of facets 28 that are shaped and positioned to face in different directions. By arranging the facets 28 in this manner and allowing the edges of the facets to form generally pointed ridges, the second surface 22 may be shaped to generally mimic masticatory surfaces of teeth within a dental arcade. Accordingly, the facets 28 will provide the user with some assistance in eating while wearing the dental splint 10. It is contemplated that the facets may be formed along substantial portions of the second surface 22 or only in certain locations as depicted in FIG. 8.

Regardless of the embodiment of dental splint 10 worn by the user, it will be preferred that the user wear the dental splint 10 continuously for a period of at least 7-10 days. Of course this duration will vary from individual to individual and from injury to injury. However, it is contemplated that the present invention will be used and practiced contemporaneously with the care and treatment of the user's dentist. The dental splint 10 may be removed after routine examination of the dental splint 10 has indicated that the avulsed tooth has attained a generally firm reattachment. However, if a period of 10 or more days passes and the avulsed tooth 2 has not attained a generally firm reattachment, reimplantation of the avulsed tooth 2 may not be possible.

In the drawings and in the specification, there have been set forth preferred embodiments of the invention and although specific items are employed, these are used in a generic and descriptive sense only and not for purposes of limitation. Changes in the form and proportion of parts, as well as a substitution of equivalents, are contemplated as circumstances may suggest or render expedient without departing from the spirit or scope of the invention as further defined in the following claims.

Thus it can be seen that the invention accomplishes at least all of its stated objectives.

I claim:

1. A method for reimplanting one or more avulsed teeth of an individual, the method comprising the steps of:
   inserting the one or more avulsed teeth into sockets, from where the one or more avulsed teeth were avulsed;
   providing a dental splint having first and second generally opposite surfaces; said first surface being pre-shaped to have a channel that is generally shaped and sized to releasably receive at least a portion of an upper or lower arcade of teeth that includes the one or more avulsed teeth;
   coupling said dental splint into an engagement position with at least a portion of said upper or lower arcade of teeth that includes the one or more avulsed teeth without bonding said splint to the avulsed teeth;
   substantially retaining said dental splint in said engagement position until a generally firm reattachment of at least one of the one or more avulsed teeth occurs; and
   applying an adhesive between said at least a portion of said upper or lower arcade of teeth and the channel of said dental splint.

2. A method for reimplanting one or more avulsed teeth of an individual, the method comprising the steps of:
   inserting the one or more avulsed teeth into sockets, from where the one or more avulsed teeth were avulsed;
   providing a dental splint having first and second generally opposite surfaces; said first surface being pre-shaped to have a channel that is generally shaped and sized to releasably receive at least a portion of an upper or lower arcade of teeth that includes the one or more avulsed teeth;
   coupling said dental splint into an engagement position with at least a portion of said upper or lower arcade of teeth that includes the one or more avulsed teeth without bonding said splint to the avulsed teeth;
   substantially retaining said dental splint in said engagement position until a generally firm reattachment of at least one of the one or more avulsed teeth occurs;
   said channel being shaped to have opposing side walls and a bottom wall that extends between lower end portions of said side walls;
   said dental splint being comprised of a substantially rigid material;
   said dental splint being coupled to said upper or lower arcade of teeth in a sufficiently secure manner that permits the individual to eat and drink while said dental split is coupled to said upper or lower arcade of teeth without unintentionally uncoupling said dental splint from said upper or lower arcade of teeth;
   periodic pressure being applied by the individual against the second surface of said dental splint after said dental splint is coupled in said engagement position; and
   adhesive being applied between said at least a portion of said upper or lower arcade of teeth and the channel of said dental splint without applying the adhesive to the one or more avulsed teeth.

3. A method for reimplanting one or more avulsed teeth of an individual, the method comprising the steps of:
   inserting the one or more avulsed teeth into sockets, from where the one or more avulsed teeth were avulsed;
   providing a dental splint having first and second generally opposite surfaces; said first surface being pre-shaped to have a channel that is generally shaped and sized to releasably receive at least a portion of an upper or lower arcade of teeth that includes the one or more avulsed teeth;
   coupling said dental splint into an engagement position with at least a portion of said upper or lower arcade of teeth that includes the one or more avulsed teeth without bonding said splint to the avulsed teeth;
   substantially retaining said dental splint in said engagement position until a generally firm reattachment of at least one of the one or more avulsed teeth occurs;
   the first surface of said dental splint being comprised of a layer of a deformably resilient material which defines a substantial portion of said groove;
   the second surface of said dental splint being comprised of a generally rigid layer of material which forms a substantial portion of said second surface; and
   adhesive being applied between said at least a portion of said upper or lower arcade of teeth and the channel of said dental splint without applying the adhesive to the one or more avulsed teeth.

* * * * *